(12) United States Patent
Berg et al.

(10) Patent No.: US 10,959,877 B2
(45) Date of Patent: Mar. 30, 2021

(54) DEVICE AND METHOD FOR REDUCING THE BODY CORE TEMPERATURE OF A PATIENT FOR HYPOTHERMIA TREATMENT BY COOLING AT LEAST TWO BODY PARTS OF THE PATIENT

(71) Applicant: BrainCool AB, Lund (SE)

(72) Inventors: Jon Berg, Dalby (SE); Christian Strand, Staffanstorp (SE); Martin Waleij, Lund (SE)

(73) Assignee: BrainCool AB, Lund (SE)

( * ) Notice: Subject to any disclaimer, the term of this patent is extended or adjusted under 35 U.S.C. 154(b) by 784 days.

(21) Appl. No.: 15/519,406

(22) PCT Filed: Oct. 15, 2015

(86) PCT No.: PCT/EP2015/073910
§ 371 (c)(1),
(2) Date: Apr. 14, 2017

(87) PCT Pub. No.: WO2016/059167
PCT Pub. Date: Apr. 21, 2016

(65) Prior Publication Data
US 2017/0224529 A1 Aug. 10, 2017

(30) Foreign Application Priority Data
Oct. 15, 2014 (SE) ........................ 1451236
Oct. 15, 2014 (SE) ........................ 1451237

(51) Int. Cl.
*A61F 7/00* (2006.01)
*A61F 7/02* (2006.01)

(52) U.S. Cl.
CPC .............. *A61F 7/0053* (2013.01); *A61F 7/02* (2013.01); *A61F 2007/0002* (2013.01); *A61F 2007/0008* (2013.01); *A61F 2007/0011* (2013.01); *A61F 2007/0056* (2013.01); *A61F 2007/0086* (2013.01); *A61F 2007/0093* (2013.01); *A61F 2007/0096* (2013.01)

(58) Field of Classification Search
CPC combination set(s) only.
See application file for complete search history.

(56) References Cited

U.S. PATENT DOCUMENTS

| 5,891,134 A * | 4/1999 | Goble ................... A61B 18/08 |
| | | 606/191 |
| 7,089,995 B2 * | 8/2006 | Koscheyev .......... A41D 13/005 |
| | | 165/46 |
| 2002/0128698 A1 * | 9/2002 | Dobak, III ............. A61B 18/02 |
| | | 607/105 |
| 2007/0255362 A1 * | 11/2007 | Levinson .................. A61F 7/10 |
| | | 607/96 |
| 2009/0131835 A1 | 5/2009 | Voorhees et al. |
| 2010/0087900 A1 | 4/2010 | Flint |

(Continued)

FOREIGN PATENT DOCUMENTS

| JP | 2005518837 A | 6/2005 |
| JP | 2006514563 A | 5/2006 |

(Continued)

*Primary Examiner* — Kaitlyn E Smith
*Assistant Examiner* — Yasamin Ekrami
(74) *Attorney, Agent, or Firm* — Capitol City TechLaw (57) ABSTRACT

A medical cooling device and a method for operating the same are provided.

16 Claims, 1 Drawing Sheet

(56) References Cited

U.S. PATENT DOCUMENTS

2013/0325089 A1* 12/2013 Divani .................. A61F 7/0085
607/104
2014/0222121 A1* 8/2014 Spence ................ A41D 13/005
607/104

FOREIGN PATENT DOCUMENTS

| JP | 2013533079 A | 8/2013 |
|----|--------------|--------|
| WO | 9944552 A1 | 9/1999 |
| WO | 02055129 A2 | 7/2002 |
| WO | 2003071999 A1 | 9/2003 |
| WO | 2004054470 A2 | 7/2004 |
| WO | 2012020267 A1 | 2/2012 |
| WO | 2013013059 A1 | 1/2013 |
| WO | 2014151872 A2 | 9/2014 |

* cited by examiner

DEVICE AND METHOD FOR REDUCING THE BODY CORE TEMPERATURE OF A PATIENT FOR HYPOTHERMIA TREATMENT BY COOLING AT LEAST TWO BODY PARTS OF THE PATIENT

This application claims priority under 35 USC 119(a)-(d) to SE patent application Nos. 1451236-2 and 1451237-0, both of which were filed on Oct. 15, 2014, the entire contents of both of which are incorporated herein by reference.

TECHNICAL FIELD

The present invention pertains to a medical cooling device and method for reducing the body core temperature of a patient, and in particular the brain of the patient, in a non-invasive manner.

CROSS-RELATED APPLICATIONS

The co-pending international application PCT/EP2015/073918, titled "Device And Method For Reducing The Body Core Temperature Of A Patient For Hypothermia Treatment", filed on Oct. 15, 2015, and claiming priority from SE1451237-0 filed on Oct. 15, 2014, is incorporated by reference in its entirety.

BACKGROUND

Medical cooling of parts of the human body for reducing the body core temperature for hypothermia treatment is a useful tool to reduce adverse impacts on the same under certain conditions. For example, medical cooling may be used for cooling the brain of patient suffering from a stroke. By reducing the temperature of the brain the risk of tissue damage is reduced for those parts of the brain lacking an adequate oxygen supply during the stroke. Another application of medical cooling is to cool the scalp for patients going through chemo therapy, to avoid undesirable hair loss.

In animal models of stroke, target temperatures of between 24° C. and 34° C. are most efficacious for reducing infarct size. However, even a brain temperature of 35° C. reduces the infarct volume by 30%. Cooling to levels of 32° to 34° C. generally requires sedation, mechanical ventilation and admission to an intensive care unit. Owing to the limited availability of intensive care beds in most countries, treatment of even a minority of acute stroke patients to those levels is therefore precluded by substantial practical and logistical problems. Temperature reductions to 35.5° C. or 35.0° C. have been shown to be feasible and safe in awake patients with acute ischemic stroke by surface cooling, in combination with for example pethidine to prevent shivering. Some studies of patients with severe traumatic brain injuries indicate that temperatures of 35 to 35.5° C. seem to be the optimal temperature at which to treat patients with severe traumatic brain injuries.

A more versatile medical cooling device and method further improving the medical cooling process of reducing the body core temperature would be advantageous.

SUMMARY

An object of the present invention is to eliminate or alleviate at least one of the drawbacks mentioned above, which is achieved by assigning to the device the characteristics according to claim 1.

According to a first aspect, a medical cooling device for conducting a non-invasive medical cooling process for reducing the body core temperature of a patient by cooling at least two body parts of a patient is provided. The medical cooling device comprises a cooling fluid supply source. Moreover, the medical cooling device comprises at least two inlet/outlet pairs, each inlet/outlet pair comprising an outlet being connected to the cooling fluid supply source and arranged for connection to one individual supply line for supplying a flow of cooling fluid from the cooling fluid supply source to a patient, and an inlet for connection to an individual return line being operatively coupled with the individual supply line and to the cooling fluid supply source thereby forming a continuous loop cooling circuit in use. The medical cooling device further comprises a flow pump connected to each inlet/outlet pair for pumping cooling liquid from the cooling fluid supply source to each of the outlets and receiving returning cooling fluid via each of the inlets. Furthermore, the medical cooling device comprises a control unit arranged to distribute different cooling power to each cooling circuit by adapting at least one control process parameter for each cooling circuit and re-starting the medical cooling process according to said adapted control process parameter.

In a second aspect a control unit is provided for distributing different cooling power to at least two body parts of a patient by adapting at least one control process parameter of a medical cooling process, wherein each body part is cooled individually by means of one cooling circuit being operatively connected to a medical cooling device. The at least one control process parameter relates to:

the operation of at least one flow control valve arranged in each cooling circuit, whereby the control unit is arranged to adapt the flow in each cooling circuit by controlling said operation;

the operation of at least one flow pump operatively coupled to each cooling circuit, whereby the control unit is arranged to adapt the flow in each cooling circuit by controlling said operation; or the energy consumption of the medical cooling device, wherein the energy consumption in each cooling circuit is calculated using the following formula relating to the first law of thermodynamics:

$$Q(\text{energy}) = \dot{m} * CP(T2 - T1),$$

wherein Q is the energy, $\dot{m}$ is the mass flow of the cooling fluid in the supply line, CP represents a constant for the cooling fluid related to the specific heat at constant pressure, T1 being the temperature of the cooling fluid exiting the medical cooling device towards the patient, and T2 being the temperature of the returning cooling fluid from the patient, whereby the control unit is configured to adapt the temperature T1 according to a target energy consumption value in each cooling circuit. The control unit is further configured to re-start the medical cooling process according to the adapted control process parameter.

According to an aspect, a method for distributing different cooling power to at least two body parts of a patient by adapting at least one control process parameter of a medical cooling process is provided. Each body part is cooled individually by means of one cooling circuit being operatively connected to a medical cooling device. The at least one control process parameter relates to:

the operation of at least one flow control valve arranged in each cooling circuit, whereby the method comprises the step of adapting (21a) the flow in each cooling circuit by controlling said operation;

the operation of at least one flow pump operatively coupled to each cooling circuit, whereby the method comprises the step of adapting (21b) the flow in each cooling circuit by controlling said operation; or the energy consumption of the medical cooling device, wherein the energy consumption in each cooling circuit is calculated using the following formula relating to the first law of thermodynamics:

$$Q(\text{energy}) = \dot{m} * CP(T2 - T1),$$

wherein Q is the energy, ṁ is the mass flow of the cooling fluid in the supply line, CP represents a constant for the cooling fluid related to the specific heat at constant pressure, T1 being the temperature of the cooling fluid exiting the medical cooling device towards the patient, and T2 being the temperature of the returning cooling fluid from the patient, wherein the method comprises the step of adapting (21c) the temperature T1 according to a target energy consumption in each cooling circuit. Moreover, the method comprises the step of re-starting (22) the medical cooling process according to the adapted control process parameter.

The control unit, medical cooling device and method may be used to reduce the body core temperature of a patient during hypothermia treatment.

BRIEF DESCRIPTION OF DRAWINGS

In order to explain the invention, a number of embodiments of the invention will be described below with reference to the drawings, in which.

DESCRIPTION OF EMBODIMENTS

An idea of the present invention is to provide a medical cooling process for cooling several body parts of patient to reduce the body core temperature said patient using a single medical cooling device. More specifically, an idea is to provide simultaneous independent cooling to each body part of the patient using the single medical cooling device. In this way some body parts may be cooled to a further extent and in a different than others such as to optimize the cooling for the given patient condition. Not only will the independent cooling of body parts allow for improved cooling efficiency, but also the power consumption of the medical cooling device will be managed in the most efficient manner, e.g. by focusing more energy to the body parts requiring more cooling and vice versa.

Figure 1:
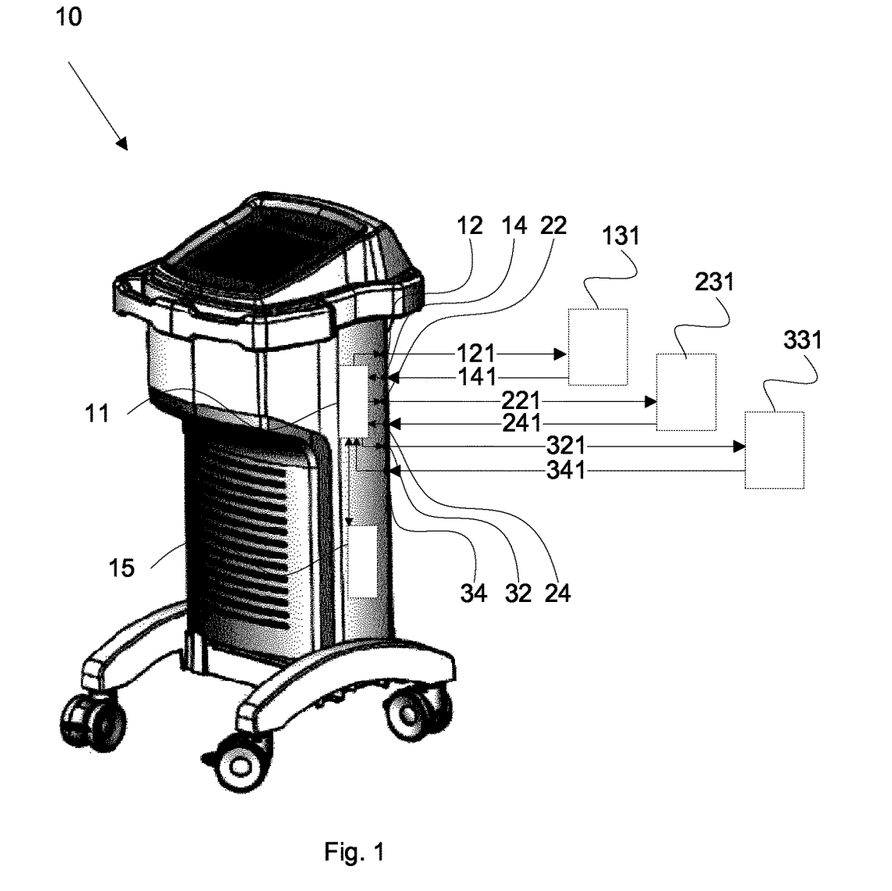
FIG. 1 is a schematic view of a medical cooling device according to one embodiment.
Figure 2:
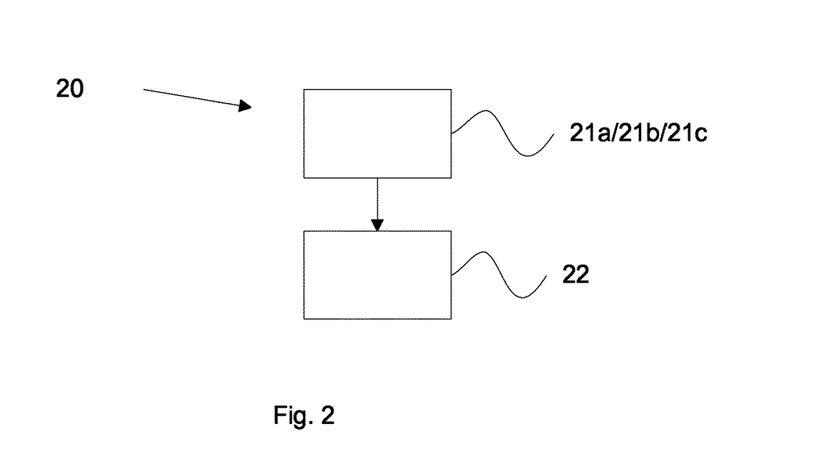
FIG. 2 illustrates a method according to an embodiment.

In an embodiment, according to FIG. 1, a medical cooling device 10 is provided. The medical cooling device 10 comprises a cooling fluid supply source 11 (schematically shown in FIG. 1 with dotted lines). The medical cooling device 10 comprises a first outlet 12 for connection to a first supply line 121 for supplying a flow of cooling fluid from the cooling fluid supply source to a patient. The medical cooling device further comprises a first inlet 14 for connection to a first return line 141 being operatively connected to the first supply line 121 returning the cooling fluid from the patient to the cooling fluid supply source 11. The first supply line 121 and the first return line 141 together form part of a first cooling circuit and may comprise tubes for the transfer of cooling fluid. A second outlet 22 of the medical cooling device is arranged to connect to a second supply line 221 and a second inlet 24 of the medical cooling device is arranged to connect to a second return line 241. The second supply line 221 and the second return line 241 together form part of a second cooling circuit and may similarly to the first cooling circuit comprise tubes for the transfer of cooling fluid.

The medical cooling device may contain a single cooling supply source 11. This is possible since the cooling rate is rather slow, e.g. 0.5 to 1.5° C./hour. The medical cooling device is provided for safely conducting hypothermia treatment wherein the body core temperature of the patient is slowly reduced from around 37 degrees to around 35 degrees, to reduce tissue damage as far as possible, e.g. when the patient has suffered from a stroke. An important factor to consider in medical devices associated with hypothermia treatment is that the cooling process needs to take some time such as not to stress the body of the patient. For improved efficiency one should also consider providing the non-invasive cooling fluid of the medical device as close to the large blood vessels in the body, e.g. via non-invasive fluid distribution devices 131, 231, 331.

Between the first supply line 121 and the first return line 141 a first cooling fluid distribution device 131, e.g. a wearable garment, which distributes the supplied cooling fluid around the body part of the body to be cooled is used.

In use, a second cooling fluid distribution device 231 is provided between the second supply line 221 and the second return line 241.

In an embodiment, at least a third outlet 32 of the medical cooling device is arranged for connection to a third supply line 321 and a third inlet 34 of the medical cooling device is arranged to connect to a third return line 341. The third supply line 321 and the third return line 341 together form part of a third cooling circuit and may similarly to the first or second cooling circuit comprise tubes for the transfer of cooling fluid. In use, a third cooling fluid distribution device 331 is provided between the third supply line 321 and the third return line 341.

Generally, each cooling fluid distribution device 131, 231, 331 may contain a channel pattern for improving the cooling efficiency of the body part to which it is connected in use. Preferably, each cooling fluid distribution device has a shape being configured to encompass and tightly fit the body part of the patient to be cooled. The cooling of the body part of the patient is thus governed by means of conductive heat transfer between the cooling fluid in the corresponding distribution device and the body part of the patient to the cooled. Hence, the cooling of the body part of the patient is preferably made ex vivo whereby there is no direct contact between the cooling fluid and the body part of the patient to be cooled.

The fluid distribution devices 131, 231, 331 are non-invasive. Normally each fluid distribution device is applied onto the patient's skin for cooling the body core temperature from outside of the body.

Ideally, the liquid cooling distribution device is preferably made of a material showing good heat conductive properties and comfortable fit in use. While metals have very good heat conductive properties, they are less suitable too allow for a comfortable fit on the body part. According to one embodiment, the at least one fluid distribution device is made of a silicon material which allows for a very comfortable fit however, having less heat conductive properties than a metal.

Depending on the type of material the temperature of the cooling fluid cooling supply source may be altered. For example, the temperature of the cooling fluid in the supply source when the distribution device is made of a silicon material may be between −9° C. and −6° C., such as −7° C. For a distribution device material having better (compared to silicon) heat conductive properties the temperature of the cooling fluid in the supply source may be higher than −6° C., such as −2° C., or even higher such as 4 till 5° C. Depending on the type of condition the patient is in, more than one distribution device may be connected to the medical cooling device. Each distribution device is supplied using a separate cooling circuit, i.e. a separate supply line and a separate return line.

It should be appreciated that the present invention is not limited to cooling fluid temperatures of −9 to −6° C. in the supply source. For some applications, e.g. where the cooling is continuously executed over prolonged period, e.g. hours, the set fluid temperature in the cooling fluid supply source may be between +3 and +6° C., such as +4° C. A higher set fluid temperature in the cooling fluid supply source may reduce or avoid the risk of tissue frost damages, which may lead to nerve damage, during prolonged continuous cooling.

In an embodiment, the first non-invasive cooling fluid distribution device 131 is arranged to be connected to the scalp of the patient. The second non-invasive cooling fluid distribution device 231 is arranged to be connected to the neck region of the patient, e.g. for cooling of the carotid artery. The third cooling non-invasive fluid distribution device 331 is arranged to be connected to the groin part of the patient.

In an embodiment, the medical cooling device is semi-portable and contains a battery in order to allow the cooling system to run for 2-3 hours without access to a socket. This makes it possible to start the cooling treatment in the emergency room (or already in the ambulance) and continuing the cooling treatment during a couple of hours when a patient with for example stroke is moved around in the hospital before being placed in a bed in a hospital ward with access to a power socket.

The cooling fluid supply source 11 may be integral with or connected to a refrigerator unit (not shown) for cooling the cooling fluid to a certain preset temperature.

The cooling fluid in the patient cooling circuit, i.e. flowing from the medical cooling device through each supply line, distribution device, return line and then back to the medical cooling device may be a conventional refrigerator liquid, such as a glycol based solution or optionally water. In the event the refrigerator unit utilizes a compressor for cooling the cooling fluid in the supply source, the compressor cooling circuit being separate from the patient cooling circuit may be using a conventional compressor refrigerant.

The medical cooling device 10 may further comprise a flow pump for providing flow rate of the cooling fluid in the cooling circuit according to the demand.

It is possible to have a single flow pump for each cooling circuit. Optionally, a single flow pump supplying flow to each of the cooling circuits may be provided, as the flow in each cooling circuit could be adapted by the operation of flow control valves as further elucidated below.

Each outlet 12, 22, 32 may be operatively coupled to the flow pump by means of internal tubes (not shown) inside the medical cooling device.

Two main factors affecting the cooling efficiency of the body part of the patient are the fluid flow rate and the temperature of the cooling fluid leaving the medical cooling device via the supply line 12. Increased flow for any cooling fluid temperature being below the temperature of the body part of the patient results in a higher rate of cooling.

Similarly, for a constant flow rate any reduction in the cooling fluid temperature leaving the medical cooling device will result in a higher rate of cooling of the body part.

In an embodiment, the medical cooling device 10 further comprises means for simultaneously adapting at least one control process parameter for each cooling circuit and re-starting the medical cooling process according to said adapted control process parameter.

The means may comprise a control unit for controlling the operation of devices of the medical cooling device, in order to adapt the flow and/or temperature of cooling fluid in each cooling circuit. The control unit comprises a processor and a memory and is thus capable of computer processing capabilities.

Flow Control Valves

In an embodiment, the control process parameter relates to the operation of at least one flow control valve arranged in each cooling circuit, whereby the control unit is configured to adapt the flow in each cooling circuit by controlling said operation. In one embodiment the flow control valve is of an ON/OFF type, e.g. solenoid being provided downstream the flow pump. In an ON position the flow of the cooling circuit allows for the rated flow of the flow pump is supplied to the supply line. In an OFF position no flow is supplied to the supply line whereby, the cooling fluid between the supply line and the return line is stationary. A mean flow is attained by using a precise timing schedule for each cooling circuit being stored in the control unit.

The control unit may be configured to allow for a precise flow in each supply line by means of controlling the associated flow control valves. For example, if the flow pump provides a rated flow of 6000 ml-8000/min, and the control unit is configured to provide a flow in the first supply line of 2000 ml/min flow, the flow control valve needs to be in the OFF position during 20 seconds each minute. For example, the timing schedule may define the flow control valve to be OFF in 10 times/minute with duration of 2 seconds each time. Alternatively, the flow control valve may be OFF 5 times/min with duration of 4 seconds each time in the OFF position. Alternatively, the control valve may be set to OFF once during 20 seconds per minute.

In an embodiment, the timing schedule of the ON/OFF valve(s) may be changed throughout the cooling treatment. For example, the ON/OFF valve(s) may be open until the cooling fluid is reduced to the demanded cooling fluid temperature, e.g. −7° C. and for a predetermined time after reaching the demanded cooling temperature, after which the flow is reduced by closing the ON/OFF valve(s) according a frequency/duration governed by the timing schedule for each cooling circuit. After another predetermined time period the closing frequency/duration may be altered further if desired.

In an embodiment, the flow control valves may be proportional valves, which may be set to more than two positions for allowing different flow rates to pass depending on the position of the valve.

By operating the flow control valves the control unit may provide for independent flow rates in each of the cooling circuits, thereby allowing for the possibility of simultaneously cooling individual body parts to different extents.

For example, in the case of cooling treatment of a stroke patient, a higher flow rate may be provided to the third distribution device at the groin, than to the first and second distribution devices. This since the cooled blood in the groin cooled blood will circulate back to the heart before it reaches the brain during the next blood circulation cycle, thereby increasing its temperature during the transport. Hence, by cooling the groin body part to a higher extent, e.g. by a higher flow rate, the temperature of the blood reaching the brain during the next blood circulation cycle will be advantageously cooler.

The flow control valve(s) may be arranged internally or externally of the medical cooling device. In an embodiment, each cooling circuit has at least one flow control valve arranged within the medical cooling device. Alternatively, or in addition, a flow control valve may be externally arranged, e.g. in the supply line(s), distribution device(s), or return line(s).

Flow Pump

In an embodiment, the control process parameter relates to the operation of the at least one flow pump (not shown), whereby the control unit is configured to adapt the flow in each cooling circuit by controlling said operation.

In an embodiment, the control unit is configured to control the output flow rate of the pump by the transmission of a control signal to the pump to thereby maintain, increasing or decreasing the flow rate.

In an embodiment, the flow pump is a constant flow pump. Here the flow may be controlled using one or several flow control valves (not shown) provided in each cooling circuit.

In an embodiment, wherein the operation of the at least one flow pump is controlled by means of an ON/OFF state and flow control valves arranged to distribute output flow of the flow pump evenly between each cooling circuit.

Energy Consumption

According to an embodiment, the control process parameter relates to the energy consumption of the medical cooling device. The energy consumption in each cooling circuit may be calculated using the following formula relating to the first law of thermodynamics:

$$Q(\text{energy}) = \dot{m} * CP * (T2-T1),$$

wherein Q is the energy, $\dot{m}$ is the mass flow of the cooling fluid in the supply line, CP represents a constant for the cooling fluid related to the specific heat at constant pressure, T1 being the temperature of the cooling fluid exiting the medical cooling device via an outlet towards the patient, and T2 being the temperature of the returning cooling fluid from the patient via an inlet. In this embodiment the control unit is configured to adapt the temperature T1 according to a target energy consumption value in each cooling circuit. In combination with the operation of the flow control valves it is possible to simultaneously direct independent energy power to each of the cooling circuits.

In an embodiment, the temperature T1 may be adapted by setting an adapted target temperature TX of the cooling fluid of the cooling fluid supply source, thereby resulting in an adapted power being transferred to a refrigerator unit of the cooling fluid supply source to cool/heat the cooling fluid in the cooling fluid supply source to the adapted target temperature. If the new target temperature TX of the cooling fluid supply source is set higher then the refrigerator unit of the supply source then heats (or avoids cooling) the cooling fluid therein such as to attain the new target temperature TX. TX may be set identical to T1 provided there are no heat loss between the cooling fluid supply source and the supply line. In practice, TX may be set slightly lower than the target T1 since the cooling fluid may absorb some heat between the supply source and the supply line, due to warm components within the medical cooling device casing.

As an example, if the power consumption of the refrigerator unit is 700 W, it is possible to direct 300 W to the first distribution device, 150 W to the second distribution device and 250 W to the third distribution device, by controlling the flow in each cooling circuit and/or supply temperature.

The control unit may also be configured to limit the energy consumption proportionally to each cooling circuit upon receipt of input that the body part(s) have reached their target temperature. By proportionally is here meant proportionally to the previous power ratio or proportion. With reference to the example above, with a new target energy consumption of 500 W, the first distribution device would receive ~214 W (300 W/700 W*500 W), the second distribution device would receive ~107 W (150 W/700 W*500 W), and the third distribution device would receive ~179 W (250 W/700 W*500 W) using such a proportionally regulation made by the control unit.

The referred input could be a temperature signal from a temperature sensor being connected to the body part of interest, or the input could be user input to the medical cooling device by the treatment staff, e.g. by using a screen thereof to input relevant data to the control unit.

It should be appreciated that by adapting the flow in each cooling circuit, by operating the control flow valve(s) in each cooling circuit the power transferred to each cooling circuit may adapted as desired. Hence, for the above example where the first distribution device in the first cooling circuit is set to receive 300 W, the second distribution device in the second cooling circuit is set to receive 150 W, and the third distribution device in the third cooling circuit is set to receive 250 W to the third distribution device, the control flow valve(s) in the first cooling circuit is set more open that that of the second and third cooling circuit, and the control flow valves of the second cooling circuit is set less open than that of the first and third cooling circuit. By more open for an ON/OFF valve would mean that the control flow valve during a given time period is set in the ON position for an extended period as compared to situation before the new "more open" setting was made. By "less open" for an ON/OFF valve would mean that the control flow valve during a given time period is set in the OFF position for an extended period as compared to situation before the new "more open" setting was made. For a proportional control valve the meaning of "more open" and "less open" follows naturally.

Monitoring of the Process Parameters

In order to improve the adaption of the control process parameter(s), the control unit is configured to monitor at least one process parameter relating to the flow rate of the pump, flow rate in each cooling circuit, temperature of the cooling fluid supply source 11, supply line temp in each cooling circuit, return line temperature in each cooling circuit, and/or energy consumption of each cooling circuit.

In order to calculate the energy consumption of the refrigerator unit of the medical cooling device, each cooling circuit may be provided with a first temperature sensor for sensing the supply temperature T1 and a second temperature sensor for sensing return temperature T2. The first and second sensor of each cooling circuit is operatively coupled to the control unit 15.

In an embodiment, at least one temperature sensor is operatively connected to the control unit are provided in the cooling fluid supply source 11.

A flow meter general to all cooling circuits may be used to measure the cooling fluid flow rate downstream of the supply line. Optionally, each cooling circuit may be provided with a flow sensor, e.g. either internally arranged, i.e. within the medical cooling device, or externally arranged, e.g. in the supply line or return lines of each cooling circuit.

It should be appreciated that when on/off valves and a constant flow pump are used, a mean flow may be calculated by the control unit based on the rated flow (e.g. 2l/min) of the flow pump and the time period during which the valve is in the on and off state, respectively. When the ON/OFF flow control valves using are set to OFF the cooling fluid may be stationary in the cooling circuit. This will mean that the temperature between the supply line and the return line will be heated by the distribution device by the body heat. Hence, in this case the control unit is configured to disregard temperature indications from the supply line temperature and return line temperature indicating an increase in return line temperature until the volume of cooling fluid being stationary in the supply line, distribution device, and the return line has been flushed out setting the ON/OFF valve to ON again.

Instead of calculating the energy consumption using the above formula, the energy consumption may be measured e.g. by any conventional power consumption measuring device etc, such as an ammeter connected in series with the refrigerator unit.

Decision Process

The control unit is configured to make a decision relating as to when to adapt a control process parameter.

In an embodiment, this decision is triggered when the total power consumption, which corresponds to the total cooling effect in the cooling circuits before losses withdrawn, of the medical cooling device increases beyond a predetermined threshold.

In an embodiment, this decision is triggered when the total cooling effect in the cooling circuits, of the medical cooling device increases beyond a predetermined threshold.

In one embodiment, this decision may be triggered by detecting a state of involuntary shivering in the patient. At the onset of involuntary shivering the body of patient starts attempts to increase the body temperature. This results in increased return line temperature, thereby increasing the power consumption, i.e. the cooling power effect, of the medical cooling device for any constant flow rate.

The table below illustrates an example of the power transferred to each cooling circuit in a medical cooling device throughout a treatment duration of 240 minutes for a patient suffering from a stroke. In this example, three cooling circuits are shown. In the first cooling circuit a cap shaped distribution device is provided for cooling the scalp of the patient. In the second cooling circuit a neck shaped distribution device is provided for cooling at least the carotid artery of the patient. In the third cooling circuit a body shaped distribution device is provided for cooling another part of the body, such as the stomache and/or groin parts of the patient.

| Time [minutes] | Total cooling effect [W] | Power to the CAP [W] | Power to the NECK COLLAR [W] | Power to the BODY PAD [W] | Core Temp. [° C.] | Brain Temp. [° C.] |
|---|---|---|---|---|---|---|
| 0 | 101 | 25 | 15 | 61 | 37 | 37 |
| 20 | 108 | 30 | 15 | 63 | 36.7 | 36.7 |
| 40 | 107 | 28 | 17 | 62 | 36.4 | 36.4 |
| 60 | 115 | 27 | 18 | 70 | 36.1 | 36.1 |
| 80 | 99 | 26 | 16 | 57 | 35.8 | 35.8 |
| 100 | 97 | 27 | 17 | 53 | 35.5 | 35.5 |
| 120 | 259 | 120 | 75 | 64 | 35.5 | 35 |
| 140 | 268 | 115 | 80 | 73 | 35.5 | 35 |
| 160 | 220 | 117 | 75 | 28 | 35 | 34.5 |
| 180 | 210 | 118 | 68 | 24 | 35 | 34 |
| 200 | 215 | 120 | 72 | 23 | 35 | 33.5 |
| 220 | 210 | 122 | 65 | 23 | 35 | 33.5 |
| 240 | 221 | 123 | 69 | 29 | 35 | 33.5 |

As may be observed from the above table, after 120 minutes from the start of the cooling treatment the total cooling effect is drastically increased to 259 W from 97 W at 100 minutes. This indicates the onset of shivering. The shivering state remains at the 140 minutes mark. At the onset of shivering the control unit is configured to adapt the flow rate in each cooling circuit. As may be observed at the 120 minutes mark the cooling power supplied to the first distribution device (cap) is increased from 27 W at the 100 minute mark to 120 W at the 120 minute mark, by increasing the flow in the first cooling circuit. Also the flow rate in the second cooling circuit (neck) is increased at the 120 minute mark thereby generating a cooling power of 75 W, which is an increase from 17 W at the 100 minute mark. The cooling power supplied to the third cooling circuit (body) remains essentially constant at the onset of shivering at the 120 minute mark. The changed power cooling effect supplied to each cooling circuit at the onset of shivering results in that the brain and the neck portion of the patient is cooled locally to a higher extent than the body portion, which thereby reduces the overall shivering state of the patient. As may be noted from the 160 minute mark the core body temperature remains at 35° C., whereas the brain temperature is continuously reduced to about 33.5° C. at the 240 minutes mark. This allows for keeping the shivering state to a constant low level or even reduces the shivering state even if the brain temperature of the is continuously lowered throughout the cooling treatment process.

Accordingly, when a state of shivering is taken into account by the control unit, in an embodiment and depending on the main target tissue to be cooled, e.g. the brain in a stroke condition, the cooling effect or power submitted to the distribution device(s) provided close to the target area are increased in relation compared to the fluid distribution device(s) connected further away from the main target area, such as the groin area in a stroke condition. In this way the total shivering effect of the patient may be reduced.

The table below illustrates an example of the power transferred to each cooling circuit in a medical cooling device throughout a treatment duration of 240 minutes for a patient suffering from cardiac arrest. In this example, three cooling circuits are shown. In the first cooling circuit a cap shaped distribution device is provided for cooling the scalp of the patient. In the second cooling circuit a neck shaped distribution device is provided for cooling at least the carotid artery of the patient. In the third cooling circuit a body shaped distribution device is provided for cooling another part of the body, such as the stomache and/or groin parts of the patient.

| Time [minutes] | Total cooling effect [W] | Power to the CAP [W] | Power to the NECK COLLAR [W] | Power to the BODY PAD [W] | Core Temp. [° C.] | Brain Temp. [° C.] |
|---|---|---|---|---|---|---|
| 0 | 101 | 25 | 15 | 61 | 37 | 37 |
| 20 | 108 | 30 | 15 | 63 | 36.7 | 36.7 |

-continued

| Time [minutes] | Total cooling effect [W] | Power to the CAP [W] | Power to the NECK COLLAR [W] | Power to the BODY PAD [W] | Core Temp. [° C.] | Brain Temp. [° C.] |
| --- | --- | --- | --- | --- | --- | --- |
| 40  | 107 | 28 | 17 | 62  | 36.4 | 36.4 |
| 60  | 115 | 27 | 18 | 70  | 36.1 | 36.1 |
| 80  | 99  | 26 | 16 | 57  | 35.8 | 35.8 |
| 100 | 97  | 27 | 17 | 53  | 35.5 | 35.5 |
| 120 | 259 | 62 | 45 | 152 | 35.5 | 35.5 |
| 140 | 268 | 68 | 43 | 157 | 35.5 | 35.5 |
| 160 | 105 | 30 | 15 | 60  | 35.5 | 35.5 |
| 180 | 100 | 28 | 17 | 55  | 35.5 | 35.5 |
| 200 | 92  | 27 | 18 | 47  | 35.5 | 35.5 |
| 220 | 109 | 26 | 16 | 67  | 35.5 | 35.5 |
| 240 | 92  | 27 | 17 | 48  | 35.5 | 35.5 |

As may be observed from the table, after 120 minutes from the start of the cooling treatment the total cooling effect is drastically increased to 259 W from 97 W at 100 minutes. This indicates the onset of shivering. The shivering state remains at the 140 minutes mark. Here, the control unit may reduce the flow (not shown in the table above) in each cooling circuit such as to produce a total cooling effect of around 100 W, which corresponds to the total cooling effect before the onset of shivering. As may be noted in the table, the cooling effect or power in the first, second, and third cooling circuits are different throughout the cooling treatment.

APPLICABILITY

In the normal case the medical cooling treatment may be started with a temperature of the cooling fluid in the cooling fluid supply source corresponding to the ambient temperature, e.g. being around 20° C. Hence, initially the supply source including the refrigerator unit, will require maximum power to cool the cooling fluid down to the set demand temperature of −9° C. to −6° C. or any other set temperature based on the application, as further explained above. During this time, the energy consumption will thus be high. Accordingly, the control unit may be configured to monitor the energy consumption of the refrigerator unit once the temperature of the cooling fluid supply source has reached the set demand temperature.

One body part of particular interest is the scalp of the patient, and here the distribution device may be shaped like a cap or helmet. Scalp cooling particularly advantageous for lowering the brain temperature in patients suffering of acute stroke as well as patients undergoing chemo therapy to reduce hair loss.

However, cooling of the brain may also be advantageous after cardiac arrest, in neonatal hypoxia ischemia or insomnia.

It should be appreciated that the medical cooling device, control unit, and method according to the embodiments presented herein may be used in combination with other methods for brain cooling such as infusion of cold saline or pharmacological cooling with antipyretics such as paracetamol. In the case of ischemic stroke, the medical cooling device, control unit, and method according to the embodiments presented herein may also be used in conjunction with reestablishment of cerebral perfusion.

Hypothermia with lowered brain temperature has been shown to be a robust neuroprotectant against a variety of brain injuries. Recently, a randomized crossover study showed that cooling of the frontal lobes with a scalp cooling device significantly reduced insomnia.

In usual care, the optimal target brain temperature seems to be 35.0°-35.5° C. Such low temperatures in the deep brain tissue cannot be reached with scalp cooling only. However, by adding cooling of the neck over the carotid arteries it is possible to reach the optimal brain temperature.

In an embodiment, in addition to the scalp silicon cap constituting a first distribution device, a separate neck band with temperature sensors is provided. The neck band is cooled by cooling fluid from the same cooling fluid supply source as the cap.

Brain cooling has been shown to be safe at least as long as the brain temperature stays at 34° C. or above.

The duration of brain cooling treatment may be anything from 30 minutes up to 24 hours or more. For stroke applications, treatment duration of up to at least 72 hours appears provide advantageous results. However, some suggestions have been made to provide cooling treatment for up to 11 to 14 days or more depending on the type of condition of the patient.

Although some of the embodiments above have been described in relation to a stroke application, in which cooling of the brain is advantageous. It should be noted that the embodiments of the present invention is equally useful in the case of cardiac arrest. For patient suffering from a sudden cardiac arrest, body core temperature control and cooling treatment to cause hypothermia can be a life saving intervention. This means that the body temperature of the patient is lowered to reduce the tissue damage due to lack of oxygen. Patients suffering from a cardiac arrest who receive a cooling treatment have a greater rate of survival and also have less risk of permanent injury, e.g. brain damage. Cooling treatment at cardiac arrest also protects all of the body organs, which each has different sensitivity for ischemia. For example, muscle tissue may cope with ichemia for hours whereas the brain may suffer great damage within only a couple of minutes. During cooling treatment of patients suffering from cardiac arrest it may be advantageous to reduce the body temperature to lower temperatures. According to an embodiment, the distribution device(s) may be provided one or more garments, each connected to one or more cooling circuits. In the case of cardiac arrest a larger part of the body, may be cooled down, and hence the distribution devices may cover a larger portion of the body, such as the legs, stomache area, arms, scalp and neck. In an embodiment, such a garment may be provided with a opening at the position of the heart such as to facilitate optional heart surgery, while keeping the garment on.

The invention claimed is:

1. A medical cooling device for conducting a non-invasive medical cooling process for reducing a body core temperature of a patient by cooling at least two body parts of the patient, the medical cooling device comprising:
   a cooling fluid supply source;
   at least two inlet/outlet pairs, each inlet/outlet pair including
      an outlet connected to the cooling fluid supply source and arranged for connection to one individual supply line for supplying a flow of cooling fluid from the cooling fluid supply source to the patient, and
      an inlet for connection to an individual return line being operatively coupled with the individual supply line and to the cooling fluid supply source thereby forming a continuous loop cooling circuit in use;

at least one flow pump connected to each inlet/outlet pair for pumping cooling liquid from the cooling fluid supply source to each of the outlets; and a control unit arranged to distribute different cooling power to each cooling circuit by adapting at least one control process parameter for each cooling circuit and re-starting the medical cooling process according to the adapted control process parameter;

wherein one of the at least one control process parameters relates to the energy consumption of the medical cooling device;

wherein the energy consumption in each cooling circuit is calculated using the following formula:

$$Q(\text{energy})=\dot{m}*CP(T2-T1),$$

wherein Q is the energy, $\dot{m}$ is the mass flow of the cooling fluid in the supply line, CP represents a constant for the cooling fluid related to the specific heat at constant pressure, T1 being the temperature of the cooling fluid exiting the medical cooling device through the outlet of each cooling circuit, and T2 being the temperature of the cooling fluid returning to the medical cooling device through the inlet of the corresponding cooling circuit;

wherein the control unit is further arranged to adapt the temperature T1 of each cooling circuit according to a target energy consumption in each cooling circuit.

2. The medical cooling device according to claim 1, wherein one of the at least one control process parameters relates to the operation of at least one flow control valve arranged in each cooling circuit.

3. The medical cooling device according to claim 2, wherein the at least one flow control valve of a cooling circuit is arranged within the medical cooling device.

4. The medical cooling device according to claim 2, wherein the at least one flow control valve of a cooling circuit is arranged adjacent to the inlet or outlet of the cooling circuit.

5. The medical cooling device according to claim 2, further comprising:
the individual supply lines and the corresponding individual return lines;
wherein the at least one flow control valve is arranged in at least one of the individual supply lines or the individual return lines.

6. The medical cooling device according to claim 1, wherein one of the at least one control process parameters relates to the operation of the flow pump for providing a flow of cooling fluid in each of the cooling circuits.

7. The medical cooling device according to claim 6, wherein the at least one flow control valve comprises a plurality of flow control valves;
wherein the operation of the flow pump is controlled by an ON/OFF state; and
wherein the plurality of flow control valves is arranged to distribute output flow of the flow pump evenly between each cooling circuit.

8. The medical cooling device according to claim 6, wherein the at least one flow control valve comprises a plurality of flow control valves;
wherein the operation of the flow pump is controlled by an ON/OFF state; and
wherein the plurality of flow control valves is arranged to distribute output flow of the flow pump proportionally between each cooling circuit.

9. The medical cooling device according to claim 2, wherein at least one flow control valve is an ON/OFF valve; and
wherein the control unit is arranged to continuously or intermittently set the ON/OFF valve to an OFF position for a first time period and an ON position for a second time period, thereby controlling the mean flow of cooling fluid in the corresponding cooling circuit.

10. The medical cooling device according to claim 1, further comprising a first temperature sensor for sensing the temperature T1 and a second temperature sensor for sensing the temperature T2, the first and the second temperature sensors being operatively coupled to the control unit.

11. The medical cooling device according to claim 1, wherein the control unit is configured to adapt the temperature T1 by setting an adapted target temperature of the cooling fluid of the cooling fluid supply source, thereby resulting in an adapted power being transferred to a refrigerator unit of the cooling fluid supply source to cool/heat the cooling fluid in the cooling fluid supply source to the adapted target temperature.

12. The medical cooling device according to claim 1, wherein the cooling fluid supply source is a single cooling fluid supply source.

13. The medical cooling device according to claim 1, wherein the at least one flow pump is a single flow pump provided for each cooling circuit.

14. The medical cooling device according to claim 1, wherein each individual supply line is connected to each individual return line via a fluid distribution device.

15. A control unit arranged to distribute different cooling power to at least two body parts of a patient by adapting at least one control process parameter of a non-invasive medical cooling process, wherein each body part is cooled individually by one cooling circuit being operatively connected to a medical cooling device to thereby reduce a body core temperature of the patient;

wherein the at least one control process parameter relates to:
the energy consumption of the medical cooling device, wherein the energy consumption in each cooling circuit is calculated using the following formula:

$$Q(\text{energy})=\dot{m}*CP(T2-T1),$$

wherein Q is the energy, $\dot{m}$ is the mass flow of a cooling fluid in a supply line, CP represents a constant for the cooling fluid related to the specific heat at constant pressure, T1 being the temperature of the cooling fluid exiting the medical cooling device towards the patient, and T2 being the temperature of the cooling fluid returning to the medical cooling device from the patient, whereby the control unit is configured to adapt the temperature T1 according to a target energy consumption value in each cooling circuit; and wherein the control unit is further arranged to re-start the medical cooling process according to the adapted control process parameter.

16. A method for distributing different cooling power to at least two body parts of a patient by adapting at least one control process parameter of a non-invasive medical cooling process, wherein each body part is cooled individually by one cooling circuit being operatively connected to a medical cooling device to thereby reduce a body core temperature of the patient;

wherein the at least one control process parameter relates to:

the energy consumption of the medical cooling device, wherein the energy consumption in each cooling circuit is calculated using the following formula:

$$Q(\text{energy}) = \dot{m} * CP(T2-T1),$$

wherein Q is the energy, m is the mass flow of the cooling fluid in a supply line, CP represents a constant for the cooling fluid related to the specific heat at constant pressure, T1 being the temperature of the cooling fluid exiting the medical cooling device towards the patient, and T2 being the temperature of the cooling fluid returning to the medical cooling device from the patient, wherein the method involves adapting the temperature T1 according to a target energy consumption in each cooling circuit; and wherein the method further comprises re-starting the medical cooling process according to the adapted control process parameter.

\* \* \* \* \*